United States Patent [19]

Bundy

[11] 4,119,666
[45] Oct. 10, 1978

[54] 2-DECARBOXY-2-AMINO-METHYL-9-DEOXY-9-METHYLENE-PGF-TYPE COMPOUNDS

[75] Inventor: Gordon L. Bundy, Portage, Mich.

[73] Assignee: The Upjohn Company, Kalamazoo, Mich.

[21] Appl. No.: 832,243

[22] Filed: Sep. 12, 1977

Related U.S. Application Data

[60] Division of Ser. No. 682,848, May 4, 1976, Pat. No. 4,060,534, which is a continuation-in-part of Ser. No. 651,622, Jan. 23, 1976, Pat. No. 4,051,467, which is a division of Ser. No. 556,768, Mar. 10, 1975, Pat. No. 3,950,363.

[51] Int. Cl.$^2$ .................... C07C 87/45; C07C 87/50; C07C 177/00
[52] U.S. Cl. .................... 260/563 R; 260/570.5 CA; 424/325; 424/330
[58] Field of Search ............... 360/563 R, 570.5 CA, 360/514 D

[56] References Cited

U.S. PATENT DOCUMENTS

| 691,157 | 1/1902 | Merling | 260/563 R |
|---|---|---|---|
| 2,520,015 | 8/1950 | Rohrmann | 260/563 R X |
| 2,736,746 | 2/1956 | Goldberg et al. | 260/563 R X |
| 2,805,266 | 9/1957 | Ziegler et al. | 260/563 R X |
| 3,046,280 | 7/1962 | Kralt et al. | 260/563 R X |
| 3,920,643 | 11/1975 | Just et al. | 260/563 R X |
| 3,931,299 | 1/1976 | Strike | 260/514 D |
| 3,931,323 | 1/1976 | Buchi et al. | 260/563 R X |

Primary Examiner—Floyd D. Higel
Attorney, Agent, or Firm—Robert A. Armitage

[57] ABSTRACT

This invention comprises certain analogs PGE or 11-deoxy-PGE compounds in which the carbonyl at C-9 is replaced by methylene. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

2 Claims, No Drawings

2-DECARBOXY-2-AMINO-METHYL-9-DEOXY-9-METHYLENE-PGF-TYPE COMPOUNDS

CROSS REFERENCE TO RELATED APPLICATIONS

The present application is a divisional application of Ser. No. 682,848, filed May 4, 1976, now issued as U.S. Pat. 4,060,534 on Nov. 29, 1977; which is a continuation-in-part of Ser. No. 651,622 filed Jan. 23, 1976, issued as U.S. Pat. 4,021,467 on May 3, 1977; which is a division of Ser. No. 556,768, filed Mar. 10, 1975, issued as U.S. Pat. 3,950,363 on Apr. 13, 1976.

The present invention relates to prostaglandin analogs, for which the essential material constituting disclosure therefor is incorporated by reference here from Ser. No. 682,848.

I claim:
1. A prostaglandin analog of the formula

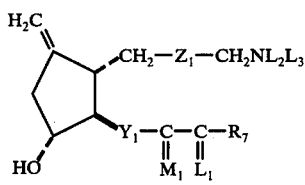

wherein $Y_1$ is trans-CH=CH—, —C≡C—, or —CH$_2$CH$_2$—;
wherein $M_1$ is

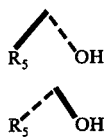

wherein $R_5$ is hydrogen or methyl;
wherein $L_1$ is

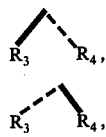

or a mixture of

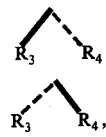

wherein $R_3$ and $R_4$ are hydrogen, methyl, or fluoro, being the same or different, with the proviso that one of $R_3$ and $R_4$ is fluoro only when the other is hydrogen or fluoro;
wherein $Z_1$ is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—(CH$_2$)$_g$—CH$_2$—,
(4) —(CH$_2$)$_3$—(CH$_2$)$_g$—CH$_2$—,
(5) —(CH$_2$)$_3$—(CH$_2$)$_g$—CF$_2$—,
(6) —CH$_2$—O—CH$_2$—(CH$_2$)$_g$—CH$_2$—,
(7) —C≡C—CH$_2$—(CH$_2$)$_g$—CH$_2$—,
(8) —CH$_2$—C≡C—(CH$_2$)$_g$—CH$_2$—,

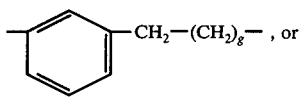

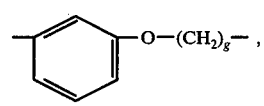

wherein $g$ is one, 2, or 3;
wherein $R_7$ is
(1) —(CH$_2$)$_m$—CH$_3$,

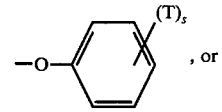

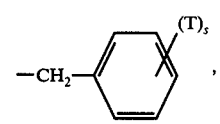

wherein $m$ is one to 5, inclusive, T is chloro, fluoro, trifluoromethyl, alkyl of one to 3 carbon atoms, inclusive, or alkoxy of one to 3 carbon atoms, inclusive and $s$ is zero, one, 2, or 3, the various T's being the same or different, with the proviso that not more than two T's are other than alkyl, with the further proviso that $R_7$ is

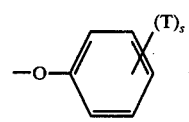

wherein T and $s$ are as defined above, only when $R_3$ and $R_4$ are hydrogen or methyl, being the same or different; and
wherein $L_2$ and $L_3$ are hydrogen or alkyl of one to 4 carbon atoms, inclusive.

2. 2-Decarboxy-2-aminomethyl-9-deoxy-9-methylene-PGF$_1$, a prostaglandin analog according to claim 1.

* * * * *

UNITED STATES PATENT OFFICE
CERTIFICATE OF CORRECTION

Patent No. 4,119,666     Dated October 10, 1978

Inventor(s) Gordon L. Bundy

It is certified that error appears in the above-identified patent and that said Letters Patent are hereby corrected as shown below:

In the Related U.S. Application Data, "Pat. No. 4,051,467" should read -- Pat. No. 4,021,467 --;

Column 1, line 30, "-C=C-" should read -- -C≡C- --;

Column 2, line 10, "-C=C-$CH_2$-" should read -- -C≡C-$CH_2$- --; line 11, "-$CH_2$-C=C-" should read -- -$CH_2$-C≡C- --.

Signed and Sealed this

Thirteenth Day of February 1979

[SEAL]

Attest:

RUTH C. MASON
*Attesting Officer*

DONALD W. BANNER
*Commissioner of Patents and Trademarks*